United States Patent [19]

Sun et al.

[11] Patent Number: 4,766,155

[45] Date of Patent: Aug. 23, 1988

[54] PROCESS FOR PRODUCING ALCOHOLS

[75] Inventors: Jui-Yuan Sun, South Holland; Erek J. Erekson, University Park, both of Ill.

[73] Assignee: Atlantic Richfield Company, Los Angeles, Calif.

[21] Appl. No.: 805,395

[22] Filed: Dec. 4, 1985

Related U.S. Application Data

[63] Continuation of Ser. No. 674,885, Nov. 26, 1984, abandoned.

[51] Int. Cl.$^4$ ............................................. C07C 27/06
[52] U.S. Cl. .................................... 518/713; 502/326
[58] Field of Search ........................................ 518/713

[56] References Cited

U.S. PATENT DOCUMENTS 4,122,110 10/1978 Sugier et al. .
4,298,354 11/1981 Hardman et al. .
4,477,594 10/1984 Greene et al. .
4,478,955 10/1984 Pesa et al. .

FOREIGN PATENT DOCUMENTS 1159435 12/1983 Canada .
1074045  9/1954 France .
 317808  8/1929 United Kingdom .
2118061 10/1983 United Kingdom .

*Primary Examiner*—Howard T. Mars
*Attorney, Agent, or Firm*—Frank J. Uxa

[57] ABSTRACT

A process for producing alcohols by reacting carbon monoxide with hydrogen in the presence of a catalyst comprising (a) copper; (b) zinc; (c) at least one element selected from the group consisting of iron, cobalt, nickel, ruthenium, thorium and mixtures thereof; and (d) at least one element selected from the group consisting of alkali metals, alkaline earth metals and mixtures thereof.

14 Claims, No Drawings

PROCESS FOR PRODUCING ALCOHOLS

This is a continuation of copending application Ser. No. 674,885 filed Nov. 26, 1984, now abandoned.

The present invention relates to a catalytic process for manufacturing alcohols, in particular relatively low molecular weight alcohols, from carbon monoxide and hydrogen.

French Pat. No. 1,074,045 proposes the use of precipitated catalysts comprising a major proportion of copper and a minor proportion of a metal of the iron group with possible addition of known activators, such as alkali metals, or zinc or chromium. Specifically, a copper, iron, potassium catalyst is described. British Pat. No. 317,808 and French Pat. No. 660,678 disclose catalysts similar to the above ones. Catalysts containing zinc and chromium with optional additives are disclosed in the Federal German Pat. No. 857,799. German Pat. No. 544,665 proposes a catalyst of alkali metals, alkaline earth metals or rare earth metals, in the absence of heavy metals. U.S. Pat. No. 4,122,110 discloses an alcohol synthesis catalyst containing four essential elements, i.e., copper, cobalt, a third metal selected from chromium, iron, vanadium and manganese, and a fourth metal—an alkali metal. Again, zinc is an optional component present in a molar amount equal to no more than 0.5 times the molar amount of cobalt present.

One problem with the prior art is that the production of alcohols from synthesis gas, e.g., mixtures of hydrogen ($H_2$) and carbon monoxide (CO) and/or carbon dioxide ($CO_2$), often results in the co-production of large amounts of water which require costly processing, e.g., extraction, distillation and the like, to remove. For example, published results (see the 11th World Petroleum Congress (Proceedings Vol. 11 p. 173 (1983)) indicate that the water content of a crude alcohol product produced with a conventional copper-cobalt catalyst may be as high as 35 weight percent. It would be advantageous to provide an alcohol synthesis catalyst and process to efficiently produce such alcohols along with reduced amounts of water.

Therefore, one object of the present invention is to provide an improved catalyst for the production of alcohols from mixtures of $H_2$ and $CO/CO_2$.

Another object of this invention is to provide an improved process for the production of alcohols from mixtures of $H_2$ and $CO/CO_2$.

A further object of the invention is to provide an improved process for the production of alcohols from mixtures of $H_2$ and $CO/CO_2$ with the co-production of reduced amounts of water. Other objects and advantages will become apparent hereinafter.

An improved process has been discovered for producing alcohols by reacting carbon monoxide (or mixtures of carbon monoxide and carbon dioxide) with hydrogen in the presence of at least one catalyst. The present process utilizes a catalyst comprising:

(a) copper (Cu)
(b) zinc (Zn)
(c) at least one element, M, selected from the group consisting of iron, cobalt, nickel, ruthenium, thorium and mixtures thereof; and
(d) at least one element, A, selected from the group consisting of alkali metal, alkaline earth metal and mixtures thereof, in the following atomic proportions: $CuZn_xM_yA_z$ where x is in the range of about 0.1 to about 5, y is in the range of about 0.005 to about 3, z is in the range of about 0.05 to about 1.0 and x is equal to more than 0.5y. Preferably, x is in the range of about 0.3 to about 3, y is in the range of about 0.01 to about 1, z is in the range of about 0.05 to about 0.5 and x is equal to more than 1.0y. Preferably, the amount of copper included in the catalyst is such that less than about 50% of all the metal atoms included in the catalyst are copper atoms.

The present process has been found to provide highly selective and productive conversion of hydrogen and carbon monoxide to methanol and other lower alcohols, preferably a mixture of such alcohols. In addition, the present process and catalyst yields a reduction effluent or product which has a reduced amount of water, e.g., relative to the amount of water produced by reacting synthesis gas to produce alcohols at a given set of reaction conditions using a conventional copper/cobalt catalyst with substantially no or reduced zinc content. In other words, the relatively high concentrations of zinc in the presently useful catalysts facilitates reduced production of water. The element M is preferably selected from the group consisting of cobalt, ruthenium and mixtures thereof, and more preferably is ruthenium.

In the process as used for the manufacture of alcohols, the $H_2$ and $CO/CO_2$ reaction preferably takes place at a pressure in the range of about 200 psig to about 4,000 psig, more preferably about 500 psig to about 2,000 psig. The mole ratio of $H_2/CO$, $CO_2$ introduced into the reaction zone is preferably in the range of about 0.4 and to about 10, more preferably about 0.5 to about 4. The reaction temperature is preferably in the range of about 300° F. to about 750° F., more preferably about 420° F. to about 700° F. The gas hourly space velocity in the reaction zone, based on the reactants introduced into the reaction zone, is preferably in the range of about 500 $hr^{-1}$ to about 20,000 $hr^{-1}$, more preferably about 2,000 $hr^{-1}$ to about 15,000 $hr^{-1}$.

Conventional and well-known catalyst manufacturing techniques may be employed to produce the presently useful catalysts. When preparing these catalytic compositions, it is preferred to employ manufacturing techniques resulting in a product having a substantially uniform or homogeneous composition. Coprecipitation techniques may preferably be used.

Shaping may be effected according to conventional techniques of the art, particularly by tabletting, or pelletting or extrusion. Drying and calcination, for example at about 500° F. to about 1800° F., are in the usual final steps.

The catalyst preferably includes at least one additional component, a support or carrier material, e.g., a porous, inorganic oxide material. The support or carrier material is more preferably selected from the group consisting of alumina, chromia, titania, lanthanum oxide, zirconia, magnesia, silica and mixtures thereof, in particular, alumina, chromia, titania, lanthanum oxide and mixtures thereof. Still more preferably the support or carrier material is selected from the group consisting of alumina, titania and mixtures thereof. Such carrier material is preferably porous, and for a surface area in the range of about 10 $m^2/gm.$ to about 600 $m^2/gm$. The carrier material preferably comprises about 1% by weight to about 90% by weight, more preferably about 10% by weight to about 50% by weight, of the total catalyst.

The support or carrier material is preferably combined with the other component of the catalyst prior to the final manufacturing steps, e.g., shaping, drying and calcining.

Examples of catalyst manufacturing methods that can be used to provide the presently useful catalysts are as follows:

The catalyst components can be coprecipitated from an aqueous mixture of metal acid salts, with a basic medium. Such acid salts include, for example, nitrates, sulfates, phosphates, halides, carbonates and the like. Water soluble metal nitrates are preferred. Any basic material having sufficient basicity to effect the above-noted coprecipitation may be employed. Preferably, the basic material is an alkali metal hydroxide dissolved in water. In certain instances, e.g., when silica, titania and/or zicronia are used as the support or carrier material, finely divided particles of these oxides can be combined with the initial aqueous mixture of the metal acid salts noted above. The finely divided oxide particles are preferably in the form of an aqueous, colloidal suspension.

An alternate method of producing the presently useful catalysts involves providing an intimate mixture of thermally decomposable salts of the desired metals and subjecting such mixture to elevated temperatures to decompose such salts. Any metal salt susceptible to thermal decomposition at the chosen temperature may be employed. Such salts may include nitrates, sulfates, phosphates, acetates, halides, carbonates, metal salts of other carbonylic acids and the like, the decomposition may occur in a reducing, oxidizing or inert environment. If a support material is employed, it may be incorporated into the initial mixture as the metal oxide. It is preferred that the catalyst have a substantially uniform composition and, therefore, it is preferred that the above-noted mixture be substantially uniformly blended. The resulting decomposed mixture can be shaped and calcined to form the final catalyst. Alternately, the original above-noted mixture can be shaped into catalyst particles before decomposition and calcination.

A further exemplary catalyst manufacturing method involves impregnating catalytic metals on the support or carrier material. Various conventional and well-known impregnation techniques are suitable for use in producing the present catalyst. For example, one or more aqueous solutions of water soluble compounds of the desired catalytic metals may be contacted with the support material to associate the desired amount of the metal with the support and carrier material. Suitable metal compounds include those listed previously. After this contacting, the contacted solid is shaped, dried and calcined to provide the final catalytic composition.

Other catalyst manufacturing methods, or combinations of methods, may be employed to provide the present compositions.

It is preferred that the catalyst be activated with a reducing medium, more preferably hydrogen and/or a combination of hydrogen and carbon monoxide, at alcohol synthesis temperature prior to using the catalyst to produce such alcohols in accordance with the present invention. In other words, it is preferred that the catalyst be in a chemically reduced state (e.g., relative to the final calcined catalyst) when used in alcohol synthesis.

The following examples are provided to better illustrate the invention, without limitation, by presenting several specific embodiments of the invention.

EXAMPLE I

A catalyst in the form of metal oxides with the metals present in the following atomic proportions:

55Cu:41Zn:10Fe:19Al:8K, was prepared by coprecipitation of an aqueous solution containing a mixture of nitrates of copper, zinc, iron and aluminum with an aqueous potassium carbonate solution. To the solution containing the suitable proportions of the metal nitrates was slowly added with vigorous agitation the potassium carbonate solution until the pH of 7 was reached. The resulting precipitate was then filtered, washed thoroughly with water, dried and calcined at 540° F. for 8 hrs. The black powdered solid was further impregnated with aqueous $K_2CO_3$ (to achieve the desired potassium concentration in the final catalyst), dried, crushed and seived through 60 mesh screen. Graphite (as a shaping lubricant) was added to the powder (2% by weight based on the powder), and the resulting mixture was pelletted.

The pelletted catalyst was activated by diluted $H_2$ in a fixed bed reactor at 450° F. Further activation was effected with pure $H_2$, then with a $H_2$-CO mixture. The synthesis of mixed alcohols was carried out by passing a gas mixture of $H_2$ and CO through an isothermal reactor containing the catalyst and solid, inert diluent. The reaction conditions were as follows:

Pressure 1,500 psig
Temperature: 520° F.
Gas Hourly Space Velocity: 4,000 hr.$-1$
Feed $H_2$/CO Molar Ratio: 2.2:1

The effluent from the reactor was cooled and the liquid products were condensed and separated from the gas phase. Gas chromatography analysis of the liquid organic products shows it contains 13% by weight of methanol and 87% by weight of higher alcohols and hydrocarbons.

EXAMPLE II

A catalyst in the form of metal oxides, with the metals present in the following atomic proportions:

55Cu:41Zn:Ru:10Cr:19Al:8K, was prepared in a manner similar to that used to produce the catalyst in Example I.

For the synthesis of mixed alcohols, the pelletted catalyst was activated by diluted $H_2$ in a fixed bed reactor at 450° F., then with pure $H_2$ and an $H_2$-CO mixture in the reactor. The operating conditions for the alcohol synthesis were as follows:

Pressure: 1,500 psig
Temperature: 650° F.
Gas Hourly Space Velocity: 2,500 hr$-1$
Feed $H_2$/CO Molar Ratio: 1:1

The liquid organic product contained 45% by weight of methanol and 55% by weight of higher alcohols and hydrocarbons.

EXAMPLE III

This example shows that it is possible to produce $CO_2$ instead of $H_2O$ as the co-product of higher alcohol synthesis by selecting appropriate catalyst formulations for practice of the present process.

A number of metal oxide catalysts were prepared by coprecipitation methods similar to that shown in Example I. When $SiO_2$ and $ZrO_2$ were used as supports, a colloidal suspension of such oxides is used instead of the corresponding nitrates to make the initial aqueous metal-nitrate solution.

The catalysts prepared in this example were activated as in Examples I and II, and were tested in an isothermal fixed bed reactor for the synthesis of mixed alcohols from a mixture of $H_2$ and CO with 2 to $1H_2$/CO molar ratio. The operating pressure was 1,500 psig. Other operating conditions and the results obtained are given in the following Table.

| Catalyst | Temp. (°F.) | Gas Hourly Space Velocity (hr-1) | Liquid Product (Wt %) | | |
|---|---|---|---|---|---|
| | | | Methanol | Higher Alcohols* | $H_2O$ |
| 55 Cu:41 Zn:10 Co:30 Al:6K | 635 | 4,000 | 73 | 24 | 3 |
| 55 Cu:41 Zn:10 Co:83 Zr:5K | 600 | 4,000 | 40 | 51 | 9 |
| 55 Cu:41 Zn:10 Co:30 Si:6K | 610 | 4,000 | 29 | 11 | 60 |
| 55 Cu:41 Zn:10 Co:30 La:6K | 620 | 4,000 | 62 | 23 | 15 |
| 55 Cu:41 Zn:10 Co:10 Mg:6K | 585 | 4,000 | 23 | 47 | 30 |

*Includes hydrocarbons

EXAMPLE IV

A catalyst in the form of metal oxides with the metals present in the following atomic proportions:

55Cu:41Zn:20Co:30Al:6K, was prepared in a manner similar to that used to produce the catalyst in Example I.

For the synthesis of mixed alcohols, the pelleted catalyst was activated by diluted $H_2$ in a fixed bed reactor at 450° F. Further activation was effected with pure $H_2$, then with a $H_2$-CO mixture. The operating conditions for mixed alcohol synthesis were as follows:
Pressure: 1,500 psig
Temperature: 624° F.
Gas Hourly Space Velocity: 4,000 hr−1
Feed $H_2$/CO Molar Ratio: 2:1

The total product yield (excluding $CO_2$) was 0.169 g/g-catalyst hr. The yield of $C_2$-$C_5$ alcohols was 0.057 g/g-catalyst hr. The selectivity to products (excluding $CO_2$) was methanol 43.8 wt.%, $C_2$-$C_5$ alcohols 33.8 wt.%, $C_6$+ alcohols >0.1 wt.%, hydrocarbons 15.6 wt.%, and water 6.8 wt.%.

EXAMPLE V

A catalyst in the form of metal oxides with the metals present in the following atomic proportions:

55Cu:41Zn:10Co:30Ti:6K, was prepared by co-precipitation in a manner similar to that used to produce the catalyst in Example I, except that the titanium was supplied to the metal nitrates solution as a colloidal suspension of titanium oxide instead of metal nitrate. Precipitation, drying and subsequent steps were carried out as in Example I.

For the synthesis of mixed alcohols, the pelleted catalyst was activated by diluted $H_2$ in a fixed bed reactor at 450° F. Further activation was effected with pure $H_2$, then with a $H_2$-CO mixture. The operating conditions for mixed alcohol synthesis were as follows:
Pressure: 1,500 psig
Gas Hourly Space Velocity: 4,000 hr−1
Feed $H_2$/CO Molar Ratio: 2:1

At 635° F. the total product yield (excluding $CO_2$) was 0.174 g/g-catalyst hr. The yield of $C_2$-$C_5$ alcohols was 0.029 g/g-catalyst hr. The selectivity to products (excluding $CO_2$) was methanol 55.9 wt.%, $C_2$-$C_5$ alcohols 16.7 wt.%, $C_6$ alcohols 13.2 wt.%, hydrocarbons 14.0 wt.%, and water 0.2 wt.%. The temperaure was subsequently raised to 660° F. where the total product yield (excluding $CO_2$) was 0.215 g/g-catalyst hr. The yield of $C_2$-$C_5$ alcohols was 0.048 g/g-catalyst hr. The selectivity to products (excluding $CO_2$) was methanol 50.2 wt.%, $C_2$-$C_5$ alcohols 22.3 wt.%, $C_6$+ alcohols 6.5 wt.%, hydrocarbons 14.5 wt.%, and water 6.5 wt.%.

These results clearly show that the present invention provides for improved synthesis of methanol and other lower alcohols. In particular, reduced water production is achieved, which can reduce the amount and cost of separation necessary to provide a useful alcohol product, for example, for use in a hydrocarbon (gasoline/diesel) fuel product.

While this invention has been described with respect to various specific examples and embodiments, it is to be understood that the invention is not limited thereto and that it can be variously practiced within the scope of the following claims.

The embodiments of this invention in which an exclusive property or privilege is claimed are defined as follows:

1. In a process for producing alcohols by reacting carbon monoxide with hydrogen in the presence of a catalyst, the improvement which comprises utilizing a catalyst consisting essentially of (a) copper (Cu); (b) zinc (Zn), (c) ruthenium (Ru); and (d) at least one element, A, selected from a group consisting of alkali metal, alkaline earth metal, and mixtures thereof, in the following atomic proportions:

Cu(Zn)x(Ru)y(A)z where:
x is in the range of about 0.3 to about 3,
y is in the range of about 0.01 to about 1,
z is in the range of about 0.05 to about 0.5, and
x is equal to more than 1.0y.

2. The process of claim 1 wherein said catalyst includes an inorganic oxide carrier.

3. The process of claim 2 wherein said carrier is selected from the group consisting of $Al_2O_3$, $Cr_2O_3$, $TiO_2$, $La_2O_3$, $ZrO_2$, MgO, $SiO_2$, and mixtures thereof.

4. The process of claim 2 wherein said catalyst includes an inorganic oxide carrier.

5. The process of claim 4 wherein said carrier is selected from the group consisting of $Al_2O_3$, $Cr_2O_3$, $TiO_2$, $La_2O_3$, $ZrO_2$, MgO, $SiO_2$, and mixtures thereof.

6. The process of claim 3 wherein said carrier is selected from the group consisting of $Al_2O_3$, $Cr_2O_3$, $TiO_2$, $La_2O_3$, and mixtures thereof.

7. The process of claim 5 wherein said carrier is selected from the group consisting of $Al_2O_3$, $Cr_2O_3$, $TiO_2$, $La_2O_3$, and mixtures thereof.

8. The process of claim 6 wherein said carrier is selected from the group consisting of $Al_2O_3$, $TiO_2$ and mixtures thereof.

9. The process of claim 7 wherein said carrier is selected from the group consisting of $Al_2O_3$, $TiO_2$ and mixtures thereof.

10. The process of claim 1 wherein the amount of copper included in said catalyst is such that less than about 50% of all the metal atoms included in said catalyst are copper atoms.

11. The process of claim 3 wherein the amount of copper included in said catalyst is such that less than about 50% of all the metal atoms included in said catalyst are copper atoms.

12. The process of claim 5 wherein the amount of copper included in said catalyst is such that less than about 50% of all the metal atoms included in said catalyst are copper atoms.

13. The process of claim 9 wherein the amount of copper included in said catalyst is such that less than about 50% of all the metal atoms included in said catalyst are copper atoms.

14. The process of claim 9 wherein the amount of copper included in said catalyst is such that less than about 50% of all the metal atoms included in said catalyst are copper atoms.

* * * * *